(12) United States Patent
Smith et al.

(10) Patent No.: US 8,591,518 B2
(45) Date of Patent: Nov. 26, 2013

(54) METHOD AND APPARATUS FOR IMPLANTING A MODULAR FEMORAL HIP

(75) Inventors: Aaron P. Smith, Warsaw, IN (US); Tyler D. Witt, Fond du Lac, WI (US)

(73) Assignee: Biomet Manufacturing, LLC, Warsaw, IN (US)

( * ) Notice: Subject to any disclaimer, the term of this patent is extended or adjusted under 35 U.S.C. 154(b) by 4 days.

(21) Appl. No.: 13/474,905

(22) Filed: May 18, 2012

(65) Prior Publication Data

US 2012/0226282 A1 Sep. 6, 2012

Related U.S. Application Data

(62) Division of application No. 12/718,018, filed on Mar. 5, 2010, now Pat. No. 8,221,432.

(51) Int. Cl.
*A61B 17/58* (2006.01)
*A61B 17/60* (2006.01)
*A61F 2/00* (2006.01)

(52) U.S. Cl.
USPC .......................................................... 606/99

(58) Field of Classification Search
USPC ........... 606/91, 99, 86 A, 86 B, 104, 914–916
See application file for complete search history.

(56) References Cited

U.S. PATENT DOCUMENTS

| | | |
|---|---|---|
| 1,714,684 A | 5/1929 | Malcolm |
| 2,231,864 A | 2/1941 | Abel |
| 3,815,599 A | 6/1974 | Deyerle |
| 4,306,550 A | 12/1981 | Forte |
| 4,549,319 A | 10/1985 | Meyer |
| 4,552,136 A | 11/1985 | Kenna |
| 4,601,289 A | 7/1986 | Chiarizzio et al. |
| 4,718,915 A | 1/1988 | Epinette |
| 4,728,333 A | 3/1988 | Masse et al. |
| 4,790,852 A | 12/1988 | Noiles |
| 4,842,606 A | 6/1989 | Kranz et al. |
| 4,883,492 A | 11/1989 | Frey et al. |
| 4,904,269 A | 2/1990 | Elloy et al. |
| 4,959,066 A | 9/1990 | Dunn et al. |
| 5,041,118 A | 8/1991 | Wasilewski |

(Continued)

FOREIGN PATENT DOCUMENTS

| | | |
|---|---|---|
| DE | 29516473 U1 | 12/1995 |
| EP | 0453695 A1 | 10/1991 |

(Continued)

OTHER PUBLICATIONS

DePuy, a Johnson & Johnson company, "Reef: Distally Interlocked Modular Femoral Reconstruction Prosthesis", 7 sheets (2004).

(Continued)

*Primary Examiner* — Sameh Boles
(74) *Attorney, Agent, or Firm* — Harness, Dickey

(57) ABSTRACT

A method of implanting a prosthetic component is disclosed that includes attaching a guide rod to the prosthetic component, removably coupling the guide rod to a shaft extending from a handle, and positioning the prosthetic component in an anatomical feature. The method also includes impacting an impaction portion of the handle and uncoupling the guide rod from the shaft, leaving the guide rod attached to the prosthetic component. The method further includes positioning a reamer over the guide rod to create a reamed opening in the anatomical feature.

19 Claims, 6 Drawing Sheets

(56) References Cited

U.S. PATENT DOCUMENTS

| | | | |
|---|---|---|---|
| 5,047,035 A | 9/1991 | Mikhail et al. |
| 5,061,271 A | 10/1991 | Van Zile |
| 5,089,004 A | 2/1992 | Averill et al. |
| 5,092,900 A | 3/1992 | Marchetti et al. |
| 5,122,146 A | 6/1992 | Chapman et al. |
| 5,201,769 A | 4/1993 | Schutzer |
| 5,211,666 A | 5/1993 | Fetto |
| 5,409,492 A | 4/1995 | Jones et al. |
| 5,468,243 A | 11/1995 | Halpern |
| 5,489,284 A | 2/1996 | James et al. |
| 5,562,666 A | 10/1996 | Brumfield |
| 5,571,111 A | 11/1996 | Aboczky |
| 5,578,037 A | 11/1996 | Sanders et al. |
| 5,601,564 A | 2/1997 | Gustilo et al. |
| 5,607,431 A | 3/1997 | Dudasik et al. |
| 5,632,747 A | 5/1997 | Scarborough et al. |
| 5,645,549 A | 7/1997 | Boyd et al. |
| 5,649,930 A | 7/1997 | Kertzner |
| 5,665,090 A | 9/1997 | Rockwood et al. |
| 5,690,636 A | 11/1997 | Wildgoose et al. |
| 5,699,915 A | 12/1997 | Berger et al. |
| 5,704,940 A | 1/1998 | Garosi |
| 5,766,261 A | 6/1998 | Neal et al. |
| 5,788,701 A | 8/1998 | McCue |
| 5,849,015 A | 12/1998 | Haywood et al. |
| 5,860,969 A | 1/1999 | White et al. |
| 5,860,982 A | 1/1999 | Ro et al. |
| 5,908,423 A | 6/1999 | Kashuba et al. |
| 5,913,860 A | 6/1999 | Scholl |
| 5,976,145 A | 11/1999 | Kennefick, III |
| 5,989,261 A | 11/1999 | Walker et al. |
| 6,022,357 A | 2/2000 | Reu et al. |
| 6,027,505 A | 2/2000 | Peter et al. |
| 6,033,405 A | 3/2000 | Winslow et al. |
| 6,110,179 A | 8/2000 | Flivik et al. |
| 6,110,211 A | 8/2000 | Weiss |
| 6,117,138 A | 9/2000 | Burrows et al. |
| 6,117,173 A | 9/2000 | Taddia et al. |
| 6,126,694 A | 10/2000 | Gray, Jr. |
| 6,136,035 A | 10/2000 | Lob et al. |
| 6,139,551 A | 10/2000 | Michelson et al. |
| 6,143,030 A | 11/2000 | Schroder |
| 6,152,963 A | 11/2000 | Noiles et al. |
| RE37,005 E | 12/2000 | Michelson et al. |
| 6,159,216 A | 12/2000 | Burkinshaw et al. |
| 6,224,605 B1 | 5/2001 | Anderson et al. |
| 6,224,609 B1 | 5/2001 | Ressemann et al. |
| 6,238,435 B1 | 5/2001 | Meulink et al. |
| 6,245,111 B1 | 6/2001 | Shaffner |
| 6,267,785 B1 | 7/2001 | Masini |
| 6,302,890 B1 | 10/2001 | Leone, Jr. |
| 6,306,174 B1 | 10/2001 | Gie et al. |
| 6,330,845 B1 | 12/2001 | Meulink |
| 6,338,734 B1 | 1/2002 | Burke et al. |
| 6,344,060 B1 | 2/2002 | Schmotzer et al. |
| 6,361,565 B1 | 3/2002 | Bonutti |
| 6,371,991 B1 | 4/2002 | Manasas et al. |
| 6,395,004 B1 | 5/2002 | Dye et al. |
| 6,468,281 B1 | 10/2002 | Badorf et al. |
| 6,517,581 B2 | 2/2003 | Blamey |
| 6,626,913 B1 | 9/2003 | McKinnon et al. |
| 6,871,549 B2 | 3/2005 | Serra et al. |
| 6,883,217 B2 | 4/2005 | Barrette et al. |
| 6,913,623 B1 | 7/2005 | Zhu |
| 6,932,819 B2 | 8/2005 | Wahl et al. |
| 7,074,224 B2 | 7/2006 | Daniels et al. |
| 7,179,259 B1 | 2/2007 | Gibbs |
| 7,210,881 B2 | 5/2007 | Greenberg |
| 7,247,171 B2 | 7/2007 | Sotereanos |
| 7,255,716 B2 | 8/2007 | Pubols et al. |
| 7,291,176 B2 | 11/2007 | Serra et al. |
| 7,296,804 B2 | 11/2007 | Lechot et al. |
| 7,297,166 B2 | 11/2007 | Dwyer et al. |
| 7,341,589 B2 | 3/2008 | Weaver et al. |
| 7,425,214 B1 | 9/2008 | McCarthy et al. |
| 7,491,242 B2 | 2/2009 | Pichon et al. |
| 7,582,092 B2 | 9/2009 | Jones et al. |
| 7,585,301 B2 | 9/2009 | Santarella et al. |
| 7,832,405 B1 | 11/2010 | Schlueter et al. |
| 7,887,539 B2 * | 2/2011 | Dunbar et al. ............ 606/86 A |
| 2003/0233100 A1 | 12/2003 | Santarella et al. |
| 2004/0107001 A1 | 6/2004 | Cheal et al. |
| 2004/0122439 A1 | 6/2004 | Dwyer et al. |
| 2004/0236341 A1 | 11/2004 | Petersen |
| 2004/0267267 A1 | 12/2004 | Daniels et al. |
| 2005/0203539 A1 | 9/2005 | Grimm et al. |
| 2007/0093844 A1 | 4/2007 | Dye |
| 2007/0123908 A1 | 5/2007 | Jones et al. |
| 2007/0129809 A1 | 6/2007 | Meridew et al. |
| 2008/0125867 A1 | 5/2008 | McCleary et al. |
| 2008/0154276 A1 | 6/2008 | Pubols et al. |
| 2008/0161811 A1 | 7/2008 | Daniels et al. |
| 2008/0208203 A1 | 8/2008 | Moindreau et al. |
| 2008/0234685 A1 | 9/2008 | Gjerde |
| 2008/0243133 A1 | 10/2008 | Heinz |
| 2008/0243190 A1 | 10/2008 | Dziedzic et al. |
| 2008/0269765 A1 | 10/2008 | Banerjee et al. |
| 2008/0294168 A1 | 11/2008 | Wieland |
| 2009/0099566 A1 | 4/2009 | Maness et al. |
| 2009/0112218 A1 | 4/2009 | McCleary et al. |
| 2009/0265014 A1 | 10/2009 | May et al. |
| 2011/0218583 A1 | 9/2011 | Smith et al. |

FOREIGN PATENT DOCUMENTS

| | | |
|---|---|---|
| FR | 2676172 A1 | 11/1992 |
| GB | 2299758 A | 10/1996 |
| WO | WO-94/21199 A1 | 9/1994 |
| WO | WO-2007106752 A2 | 9/2007 |

OTHER PUBLICATIONS

Zimmer, Inc., "Zmr Hip System", 19 sheets (2004).

B010463.0 Arcos Modular Femoral Revisions System Surgical Techniques, Biomet Orthopedics, 96 pages (2010).

* cited by examiner

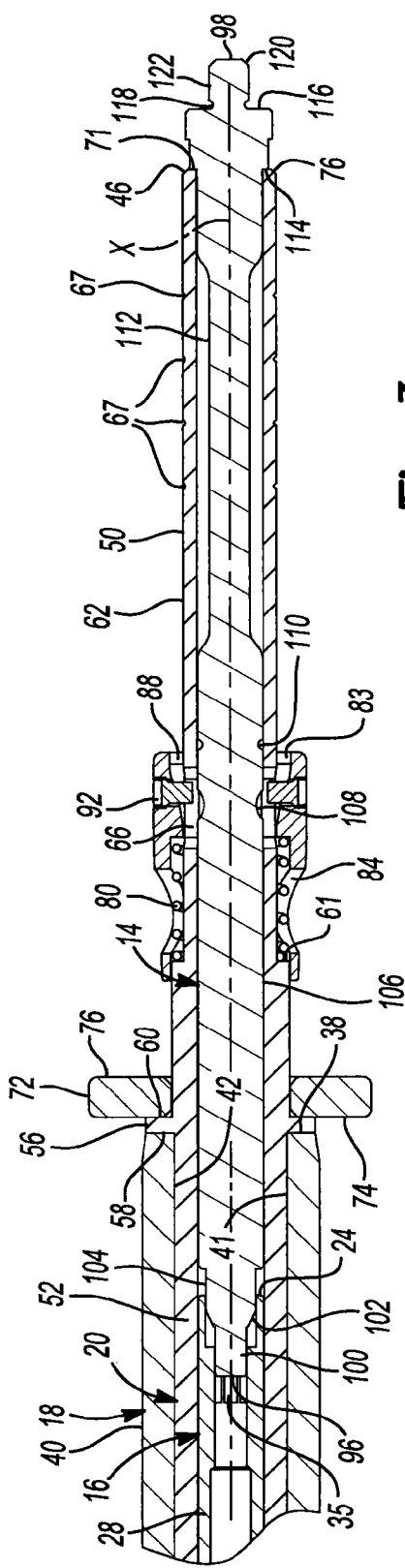
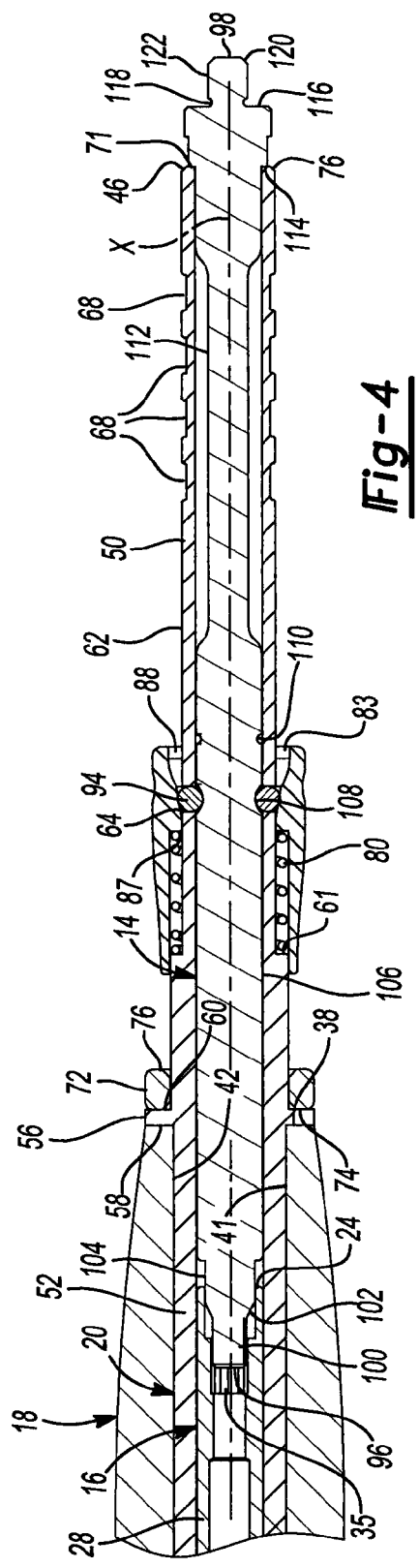

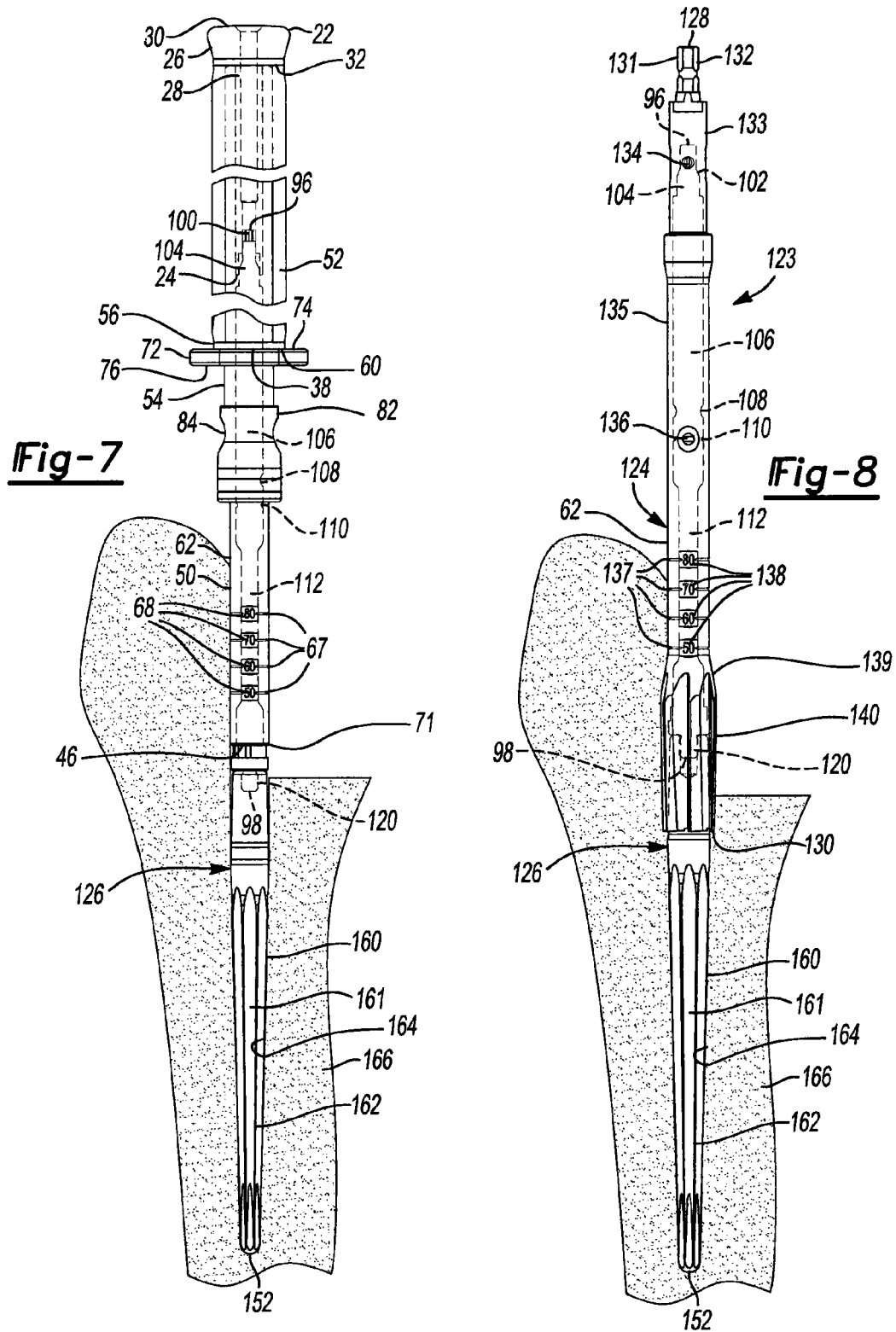

METHOD AND APPARATUS FOR IMPLANTING A MODULAR FEMORAL HIP

CROSS-REFERENCE TO RELATED APPLICATIONS

This application is a divisional of U.S. patent application Ser. No. 12/718,018, filed on Mar. 5, 2010. This application is related to U.S. patent application Ser. No. 12/718,230, filed on Mar. 5, 2010; U.S. patent application Ser. No. 12/718,023, filed on Mar. 5, 2010; U.S. patent application Ser. No. 12/718,026, filed Mar. 5, 2010; U.S. patent application Ser. No. 12/718,027, filed on Mar. 5, 2010; and U.S. patent application Ser. No. 12/718,031, filed on Mar. 5, 2010. The disclosures of each of the above applications are incorporated herein by reference.

FIELD

The following relates to an insertion tool, and more specifically, relates to an insertion system for a modular femoral revision procedure.

BACKGROUND

The statements in this section merely provide background information related to the present disclosure and does not constitute prior art.

Prosthetic joints can reduce pain due to arthritis, deterioration, deformation, and the like. Prosthetic hip joints often include a femoral component that is fixed to the patient's femur and an acetabular cup that is fixed within the patient's pelvis. More specifically, the femoral component can include a distal stem that extends into the patient's resected femur and a proximal body having a rounded head that is received within the acetabular cup. The head can articulate within the cup so as to moveably couple the femoral component within the acetabular cup.

Typically, the distal stem is first implanted in the intramedullary canal of the femur, and then a guide rod is separately attached to the distal stem. A reamer is then slid over the guide rod to partially ream a proximal portion of the femur, thereby creating a reamed opening that receives the proximal body. The guide rod ensures that the reamer is in the proper orientation such that the resultant reamed opening matches the geometry of the femoral component of the prosthetic joint. This ensures that the femoral component properly fits within and fixes to the femur.

Although insertion systems have been adequate for their intended purposes, these systems can be improved. For instance, insertion processes can be time consuming and inconvenient, especially if multiple steps are needed for inserting components of the prosthetic joint and components of the insertion system.

SUMMARY

An insertion system for implanting a prosthetic component is disclosed and includes a handle, a shaft, and a guide rod. The handle includes an impaction portion. The shaft extends from and is fixed to the handle. The guide rod is removably coupled to the shaft and includes a proximal end adapted to be rotationally fixed within the impaction portion and a distal end adapted to attach to the prosthetic component.

In another aspect, an insertion system is disclosed and includes a handle, a shaft, a guide rod, and a coupling mechanism. The handle includes an impaction portion. The shaft extends from and is fixed to the handle. The guide rod includes a proximal end adapted to be rotationally fixed within the impaction portion and a distal end adapted to attach to the prosthetic component. The coupling mechanism removably couples the guide rod to the shaft. The guide rod axially receives a reamer upon removing the guide rod from the shaft.

A method of implanting a prosthetic component is disclosed that includes attaching a guide rod to the prosthetic component, removably coupling the guide rod to a shaft extending from a handle, and positioning the prosthetic component in an anatomical feature. The method also includes impacting an impaction portion of the handle and uncoupling the guide rod from the shaft, leaving the guide rod attached to the prosthetic component. The method further includes positioning a reamer over the guide rod to create a reamed opening in the anatomical feature.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3 is a sectional view of the insertion system of FIG. 1 taken along the line 3-3;

FIG. 4 is a sectional view of the insertion system of FIG. 1 taken along the line 4-4;

FIG. 7 is a side view of the insertion system of FIG. 1 shown during an insertion procedure;

FIG. 8 is a side view of the reaming system of FIG. 5 shown during a reaming procedure.

DESCRIPTION OF VARIOUS EMBODIMENTS

Figure 1:
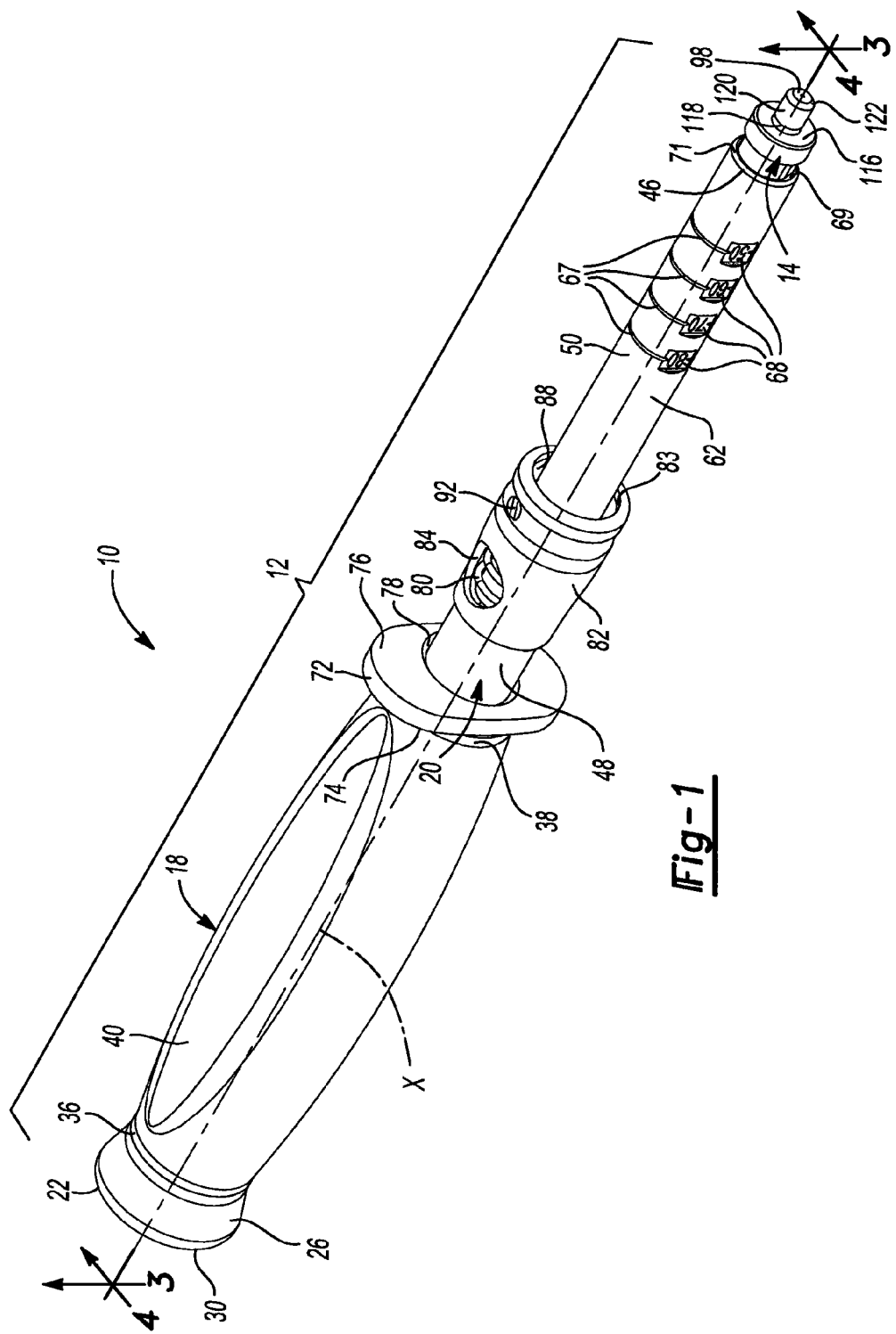
FIG. 1 is an isometric view of an exemplary embodiment of an insertion system according to various teachings of the present disclosure.
Figure 2:
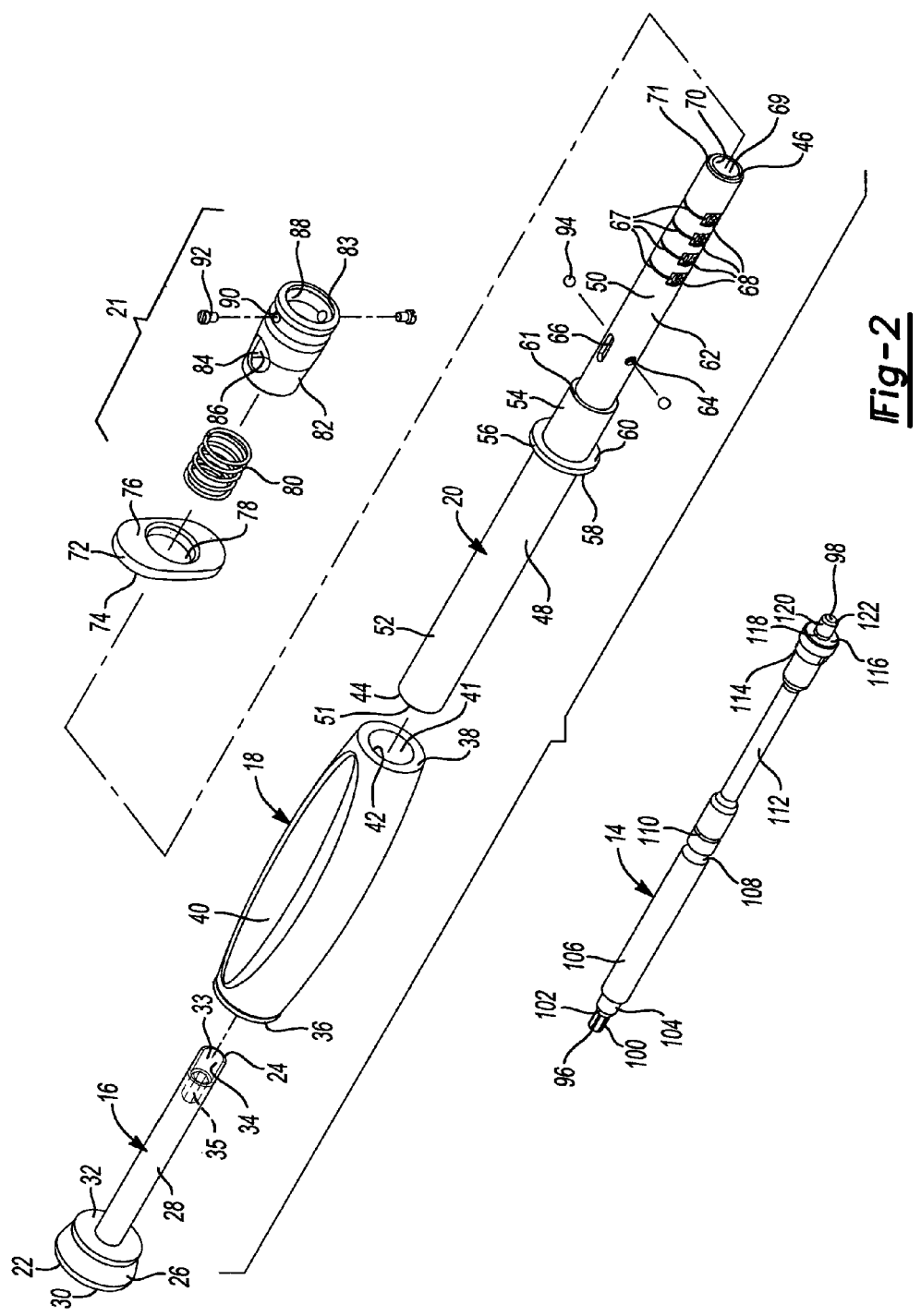
FIG. 2 is an exploded isometric view of the insertion system of FIG. 1, which includes an inserter assembly and a guide rod.

The following description is merely exemplary in nature and is not intended to limit the present disclosure, application, or uses. It should be understood that throughout the drawings, corresponding reference numerals indicate like or corresponding parts and features. Moreover, while the insertion and reaming systems described herein are described in relation to reaming an intramedullary (IM) canal of a femur, these systems can be used in any other area of a patient as well.

Referring initially to FIGS. 1 through 4, an insertion system 10 is illustrated according to various exemplary embodiments of the present disclosure. The insertion system 10 can extend along a longitudinal axis x and include an inserter assembly 12 and a guide rod 14. The inserter assembly 12 can include an impaction member 16, a handle 18, a shaft 20, and a coupling mechanism 21.

The impaction member 16 can be machined out of metal and can include a proximal end 22 and a distal end 24. The impaction member 16 can further include a rounded impaction portion 26 adjacent to the proximal end 22 and a cylindrical portion 28 adjacent to the distal end 24. The rounded impaction portion 26 can include a hemispherical surface 30 at the proximal end 22 and flat annular surface 32 opposite the hemispherical surface 30. The cylindrical portion 28 can extend from the rounded impaction portion 26 to the distal end 24. The cylindrical portion 28 can define an axially extending hole 33 that extends partially through the cylindrical portion 28. The hole 33 can define an inner cylindrical surface 34 and an inner hex surface 35.

The handle 18 can be molded from silicone and can include a proximal end 36 and a distal end 38. The handle 18 can further include elliptical grooves 40 extending along the longitudinal axis x and a hole 41 extending axially through the handle 18 from the proximal end 36 to the distal end 38. The hole 41 can define an inner cylindrical surface 42 within the handle 18.

A shaft 20 can be machined from metal and can include a proximal end 44 and a distal end 46. The shaft 20 can further include a first diameter portion 48 adjacent to the proximal end 44 and a second diameter portion 50 adjacent to the distal end 46. The first diameter portion 48 can include a flat annular surface or rim 51 at the proximal end 44 and outer cylindrical surfaces 52, 54 extending from the flat annular surface 51 toward the distal end 46 and separated by a washer 56. The washer 56 can be machined integrally with the shaft 20 or can be machined separate from the shaft 20 and later affixed to the shaft 20 through any suitable means such as welding. The washer 56 can include a flat annular surface or rim 58 facing the proximal end 44 and flat annular surface 60 facing the distal end 46. The first diameter portion 48 can further include a flat annular surface or rim 61 at the transition from the first diameter portion 48 to the second diameter portion 50.

The second diameter portion 50 can include an outer cylindrical surface 62 having holes 64 and slots 66 extending transversely through the second diameter portion 50. The holes 64 can be offset 90 degrees from the slots 66. The second diameter portion 50 can also include grooves 67 having numbered indicia 68.

The shaft 20 can also define a hole 69 that extends axially from the proximal end 44 to the distal end 46 and defines an inner cylindrical surface 70. The shaft 20 can further include a flat annular surface or rim 71 at the distal end 46 and a striker plate 72. The striker plate 72 can abut the flat annular surface 60 of the washer 56 and include a flat elliptical surface 74 that faces the proximal end 44 of the shaft 20 and a flat elliptical surface 76 that faces the distal end 46 of the shaft 20. The striker plate 72 can further include a hole 78 that extends from the flat elliptical surface 74 to the flat elliptical surface 76. The striker plate 72 can be machined separate from the shaft 20 and affixed to the shaft 20 through any suitable means such as welding.

The coupling mechanism 21 can include a spring 80 and a sleeve 82. The sleeve 82 can include an axial hole 83 extending longitudinally through the sleeve 82 and a hole 84 extending transversely through the sleeve 82. The hole 83 can define an inner cylindrical surface 86 and an inner tapered surface 88. The sleeve 82 can further include holes 90 that extend transversely through the sleeve 82 and are offset by 180 degrees from each other. The coupling mechanism 21 can further include pins or set screws 92 that are received in the holes 90 of the sleeve 82 and ball bearings 94 that are captured between the inner tapered surface 88 and the holes 64 in the shaft 20.

Upon assembly of the inserter assembly 12, the cylindrical portion 28 of the impaction member 16 can be inserted into the hole 69 of the shaft 20. The impaction member 16 can be welded to the shaft 20 at the interface between the flat annular surface 32 of the impaction member 16 and the flat annular surface 51 of the shaft 20. The handle 18 can be molded over the outer cylindrical surface 52 such that the handle 18 extends from the flat annular surface 32 of the impaction member 16 to the flat annular surface 58 of the washer 56. The striker plate 72 can be slid over the outer cylindrical surface 54 of the shaft 20 and the flat elliptical surface 76 of the striker plate 72 can be welded to the outer cylindrical surface 54 of the shaft 20.

The spring 80 can be slid over the outer cylindrical surface 62 of the shaft 20 and engage the flat annular surface 61 of the shaft 20. The sleeve 82 can also be slid over the outer cylindrical surface 62 to capture the spring 80 between the inner cylindrical surface 86 of the sleeve 82 and the outer cylindrical surface 62 of the shaft 20. The ball bearings 94 can be inserted between the inner tapered surface 88 of the sleeve 82 and the holes 64 in the second diameter portion 50 of the shaft 20. The sleeve 82 can be positioned such that the holes 90 are aligned with the slots 66 in the second diameter portion 50 of the shaft 20. The pins 92 can be inserted through the holes 90 of the sleeve 82 and into the corresponding slots 66 in the second diameter portion 50 of the shaft 20.

The guide rod 14 can be machined from metal and can include a proximal end 96, a distal end 98, and various surfaces between the proximal end 96 and the distal end 98. An outer hex surface 100 can be adjacent to the proximal end 96 and an outer tapered surface 102 can extend from the outer hex surface 100 toward the distal end 98. A first outer cylindrical surface 104 can be adjacent to the outer tapered surface 102 and extend toward the distal end 98.

A second outer cylindrical surface 106 can be adjacent to the first outer cylindrical surface 104 and extend toward the distal end 98. The second outer cylindrical surface 106 can include an annular groove 108 and an annular groove 110. The groove 108 and the groove 110 can extend around the circumference of the second outer cylindrical surface 106.

An inconstant diameter outer surface 112 can extend from the second outer cylindrical surface 106 toward the distal end 98. A flat annular surface or rim 114 can abut the inconstant diameter outer surface 112 and face the proximal end 96. A flat annular surface or rim 116 can be opposite from the flat annular surface 114 and face the distal end 98. A groove 118 can be included at the interface between the flat annular surface 116 and an outer threaded surface 120. An outer tapered or beveled surface 122 can extend from the outer threaded surface 120 to the distal end 98 of the guide rod 14.

Figure 5:
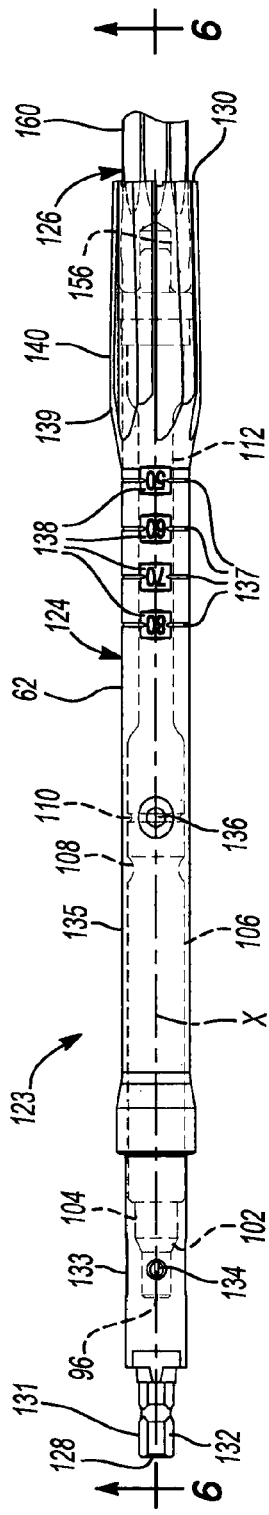
FIG. 5 is a side view of a reaming system including the guide rod of FIG. 1 attached to a distal stem and a reamer slid over the guide rod.
Figure 6:
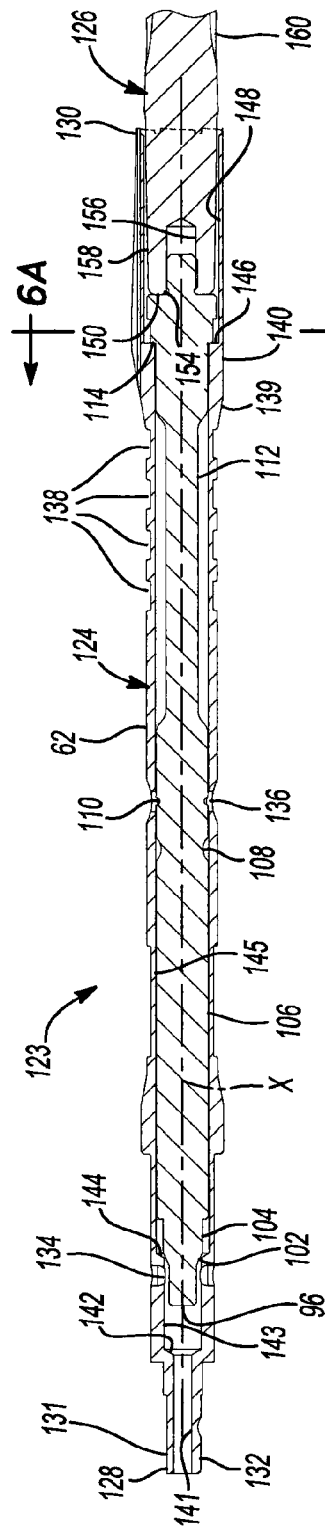
FIG. 6 is a sectional view of the reaming system of FIG. 5 taken along the line 6-6.
Figure 6A:
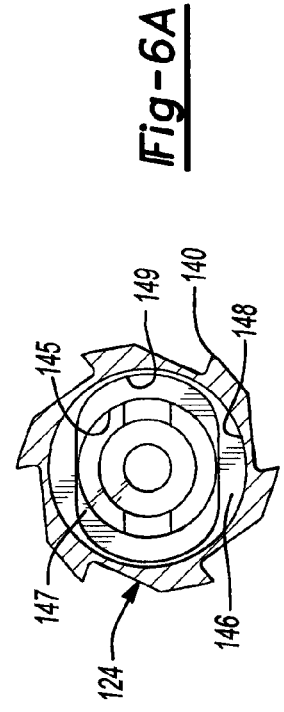
FIG. 6A is a sectional view of the reamer of FIG. 6 taken along the line 6A-6A.

Referring now to FIGS. 5 through 6A, a reaming system 123 is illustrated according to various exemplary embodiments of the present disclosure. The reaming system 123 can include the guide rod 14 and a proximal reamer 124. The guide rod 14 can be threadingly attached to a distal stem 126 prior to assembly of the reaming system 123, as will be described in more detail below.

The proximal reamer 124 can include a proximal end 128 and a distal end 130. The proximal reamer 124 can further include a first cylindrical drive portion 131 adjacent to the proximal end 128 and having an outer tri-shank surface 132. A second cylindrical portion 133 of the proximal reamer 124 can extend from the first cylindrical drive portion 131 toward the distal end 130 and include a hole 134 extending transversely through the second cylindrical portion 133. A third cylindrical portion 135 of the proximal reamer 124 can extend from the second cylindrical portion 133 toward the distal end 130 and include a hole 136 extending transversely through the third cylindrical portion 135. Grooves 137 having numbered indicia 138 can extend around the circumference of the third cylindrical portion 135. An outer tapered portion 139 of the proximal reamer 124 can extend from the third cylindrical portion 135 to the distal end 130 and include cutting flutes 140 extending along the longitudinal axis x.

The proximal reamer 124 can be canulated and include various interior surfaces between the proximal end 128 and the distal end 130. A first inner cylindrical surface 141 can extend from the proximal end 128 toward a first inner tapered surface 142. The first inner tapered surface 142 can extend from the first inner cylindrical surface 141 to a second inner cylindrical surface 143. A second inner cylindrical surface 143 can extend from the inner tapered surface 142 to a second inner tapered surface 144. The second inner tapered surface 144 can extend from the second inner cylindrical surface 143 to a third inner cylindrical surface 145.

A flat annular surface or rim 146 and a flat elliptical surface 147 can be included at the interface between the third inner cylindrical surface 145 and a fourth inner cylindrical surface 148. The flat elliptical surface 147 can extend radially from the third inner cylindrical surface 145 to an inner elliptical wall 149. The flat annular surface 146 can extend radially from the inner elliptical wall 149 to the fourth inner cylindrical surface 148. The fourth inner cylindrical surface 148 can extend axially from the flat annular surface 146 to the distal end 130. A distal reamer can be inserted into the proximal reamer 124 to ream a distal portion of a femur. The distal reamer can be axially received and rotationally fixed by the inner elliptical wall 149 and can abut the flat elliptical surface 147.

With continued reference to FIG. 6 and additional reference to FIGS. 7 and 8, the distal stem 126 can include a proximal end 150 and a distal end 152. A hole 154 can extend partially into the distal stem 126 along the longitudinal axis x. The hole 154 can define an inner cylindrical surface 156. The distal stem 126 can further include outer tapered surfaces 158, 160. The outer tapered surface 158 can taper outwards as it extends from the proximal end 150 toward the distal end 152. The outer tapered surface 160 can taper inwards as it extends from the outer tapered surface 158 to the distal end 152. The outer tapered surface 160 can include elliptical grooves 161 extending along the longitudinal axis x and splines 162 between the elliptical grooves 161.

A method of implanting the distal stem 126 using the insertion system 10 will now be described. The distal end 98 of the guide rod 14 can be attached to the proximal end 150 of the distal stem 126. The outer threaded surface 120 adjacent to the distal end 98 of the guide rod 14 can be threaded into the inner cylindrical surface 156 of the distal stem 126. The inner cylindrical surface 156 can include threads that engage the outer threaded surface 120. The outer threaded surface 120 of the guide rod 14 can be threaded into the inner cylindrical surface 156 of the distal stem 126 until the flat annular surface 116 of the guide rod 14 abuts the proximal end 150 of the distal stem 126. The distal end 98 of the guide rod 14 can be attached to the proximal end 150 of the distal stem 126 using methods other than the threaded fit described above, such as using an interference fit and/or a fastener.

The inserter assembly 12 can be placed over the guide rod 14 to thread the outer threaded surface 120 of the guide rod 14 into the inner cylindrical surface 156 of the distal stem 126. When the inserter assembly 12 is placed over the guide rod 14, the inner hex surface 35 of the impaction member 16 can act against the outer hex surface 100 of the guide rod 14 to rotate the outer threaded surface 120 of the guide rod 14 relative to the inner cylindrical surface 156 of the distal stem 126. Alternatively, other driver mechanisms that include an inner hex surface can be used to thread the guide rod 14 into the distal stem 126. Additionally, the guide rod 14 can be rotated by hand to thread the guide rod 14 into the distal stem 126.

Referring again to FIGS. 3 and 4, the guide rod 14 can be removably coupled to the shaft 20 with the distal stem 126 attached to the guide rod 14. The guide rod 14 can be inserted into the hole 69 of the shaft 20 until the flat annular surface 114 of the guide rod abuts the flat annular surface 71 of the shaft 20. The guide rod 14 can be rotated as the guide rod 14 is inserted into the hole 69 of the shaft 20 such that the outer hex surface 100 of the guide rod 14 can be inserted within the inner hex surface 35 in the cylindrical portion 28 of the impaction member 16.

The inner hex surface 35 of the impaction member 16 envelops or receives the outer hex surface 100 of the guide rod 14 to rotationally fix the guide rod 14 within the inserter assembly 12. The guide rod 14 can be rotationally fixed within the inserter assembly 12 using methods other than the hex drive fit described above, such as using an interference fit and/or a fastener. Rotationally fixing the guide rod 14 within the inserter assembly 12 provides version control to rotationally position the distal stem 126 during the implant. In addition, when the coupling mechanism 21 is in an engaged position as shown, the inner tapered surface 88 of the sleeve 82 acts against the ball bearings 94 to engage the ball bearings 94 with the groove 108 in the guide rod 14, and thereby axially fixing the guide rod 14 relative to the inserter assembly 12 in a quick release manner. The spring 80 acts against the flat annular surface 61 of the shaft 20 and flat annular surface 87 of the sleeve 82 to bias the sleeve 82 toward the distal end 46 of the shaft 20, and thereby maintain the coupling mechanism 21 in the axially engaged position.

Referring again to FIG. 7 with the guide rod 14 attached to the distal stem 126 and the guide rod 14 rotationally and axially fixed to the inserter assembly 12, the inserter assembly 12 can be used to position the distal stem 126 in an IM canal 164 of a femur 166. A hammer or other blunt instrument can be used to impact the hemispherical surface 30 on the rounded impaction portion 26 of the impaction member 16 to fit the distal stem 126 within the IM canal 164. The fit between the distal stem 126 and the IM canal 164 can be a snug fit or an interference fit. The splines 162 can grip the inner surface of the IM canal 164 to fix the distal stem 126 within the femur 166. With the guide rod 14 attached to the distal stem 126 and the distal stem 126 fixed within the femur 166, the guide rod 14 can be uncoupled from the shaft 20, thereby leaving the guide rod 14 and the distal stem 126 fixed within the IM canal 164 of the femur 166.

In some instances, the distal stem 126 can be misaligned with the IM canal 164 when the rounded impaction portion 26 of the impaction member 16 is impacted to implant the distal stem 126 within the IM canal 164. In these instances, a hammer or other blunt instrument can be used to impact the flat elliptical surface 76 on the striker plate 72 and thereby dislodge the distal stem 126 from the IM canal 164. The insertion system 10 can then be used again to implant the distal stem 126 within the IM canal 164.

Referring again to FIGS. 3 and 4, the coupling mechanism 21 can be manipulated to uncouple the guide rod 14 from the shaft 20. The sleeve 82 can be axially retracted toward the proximal end 44 of the shaft 20 such that the inner tapered surface 88 of the sleeve 82 progressively disengages the ball bearings 94 from the groove 108 and the guide rod 14. The spring 80 is compressed as the sleeve 82 is axially retracted towards the proximal end 44 of the shaft 20. In addition, the pins 92 in the holes 90 of the sleeve 82 translate within the slots 66 of the shaft 20. The inner tapered surface 88 of the sleeve 82 is sized such that the ball bearings 94 can move transversely away from the guide rod 14 when the sleeve 82 is axially retracted, but the ball bearings 94 remain captured between the inner tapered surface 88 of the sleeve 82 and the holes 64 in the outer cylindrical surface 62 of the shaft 20.

In the method of implanting a distal stem discussed above, the distal stem 126 is implanted in the IM canal 164 with the guide rod 14 attached to the distal stem 126. In conventional methods, a distal stem is first implanted in the IM canal of a femur, and then a guide rod is subsequently attached to the distal stem. Thus, the method of implanting a distal stem discussed in the present disclosure eliminates the step of attaching the guide rod to the distal stem after the distal stem is implanted in the IM canal. Eliminating this step saves time and improves convenience in a modular femoral revision procedure. Moreover, it may be difficult to attach the guide rod 14 after the distal stem 126 is implanted into the IM canal 164 of the femur 166, since the proximal end 150 of the distal stem 126 is within the bone.

Referring again to FIG. 8, a method of reaming an IM canal of a femur using the reaming system 123 will now be discussed. As discussed above, the guide rod 14 can be uncoupled from the inserter assembly 12, thereby leaving the guide rod 14 and the distal stem 126 fixed within the IM canal 164 of the femur 166. The proximal reamer 124 can then be placed over the guide rod 14 and the distal stem 126 to ream the IM canal 164.

Placing the proximal reamer 124 over the guide rod 14 ensures that the proximal reamer 124 is in proper orientation such that the resultant reamed opening matches a proximal body to be fit over the distal stem 126. The proximal reamer 124 can be slid over the guide rod 14 and the distal stem 126 until the flat annular surface 146 of the proximal reamer 124 abuts the flat annular surface 114 of the guide rod 14. The grooves 137 and numbered indicia 138 may be used to gage the depth at which the proximal reamer 124 is inserted into the IM canal 164. This depth may be used to size the proximal body to be fit over the distal stem 126.

When the flat annular surface 146 of the proximal reamer 124 abuts the flat annular surface 114 of the guide rod 14, the groove 110 in the second outer cylindrical surface 106 of the guide rod 14 is visible through the hole 136 and the proximal reamer 124. This provides a visible check to ensure that the flat annular surface 146 of the proximal reamer 124 is abutting the flat annular surface 114 of the guide rod. Then, the proximal reamer 124 can be withdrawn from the IM canal 164 and the guide rod 14 can be unthreaded from the distal stem 126. In turn, the distal stem 126 is left fixed within the IM canal 164 and the IM canal 164 includes a reamed opening matching the geometry of the proximal body that fits over the distal stem 126.

Figure 9:
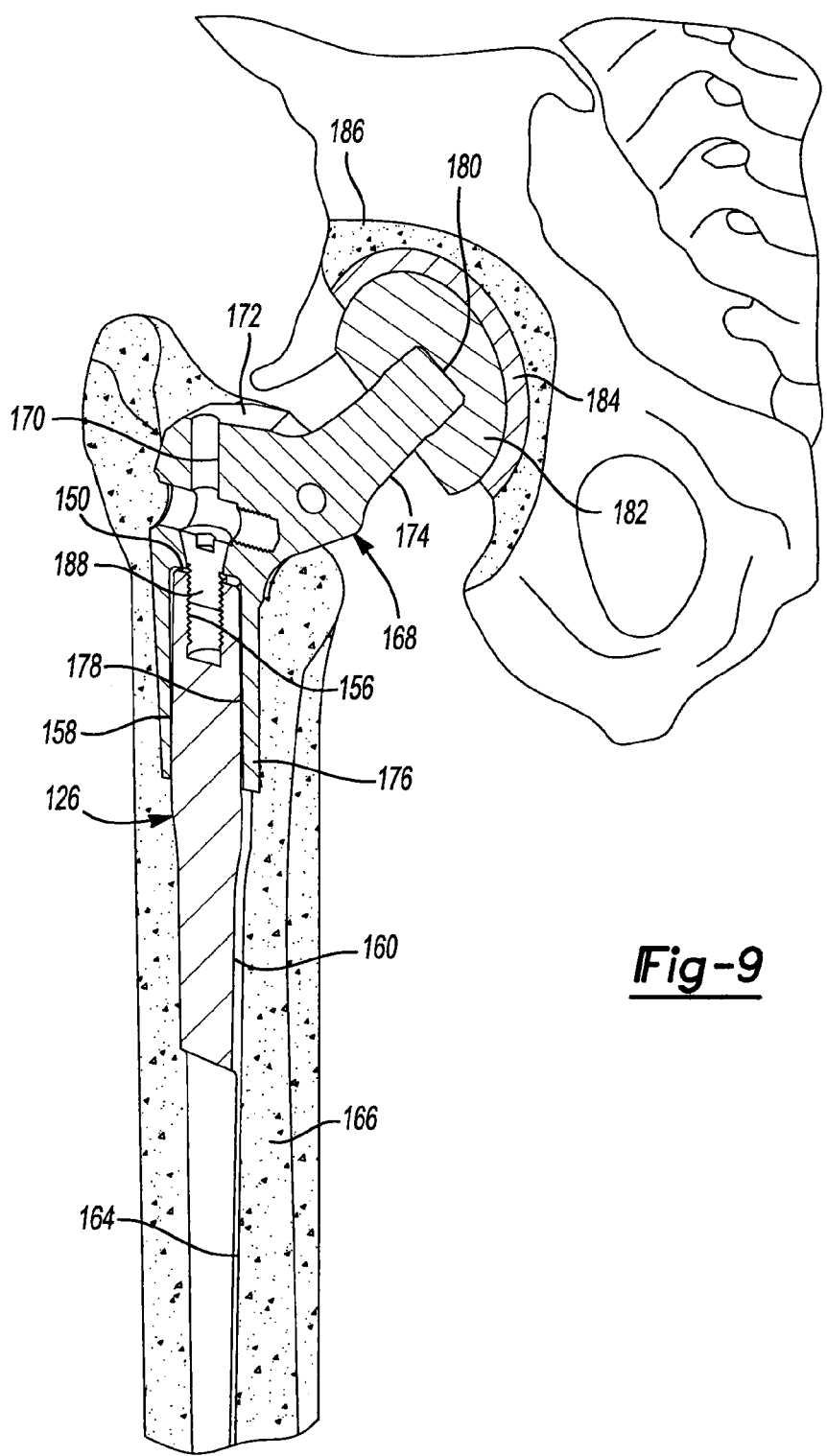
FIG. 9 is a sectioned isometric view of a proximal body attached to the distal stem of FIG. 1 and an acetabular cup that is fixed within a pelvis.

Referring now to FIG. 9, a proximal femoral body 168 can be placed over the distal stem 126 as part of a modular femoral revision procedure. The proximal femoral body 168 can include a bore 170 that extends axially from a proximal end 172. The proximal femoral body 168 can also include a neck portion 174 and a distal end 176 having an axially extending bore 178. Neck portion 174 can include a distal end 180 that is received within a femoral head 182. The femoral head 182 can mate with an acetabular cup 184 that is fixed within a pelvis 186. The distal end bore 178 can be tapered to matingly receive the outer tapered surface 158 of the distal stem 126. The proximal femoral body 168 can be coupled to the distal stem 126 with a Morse taper connection such that the outer tapered surface 158 of the distal stem 126 is press fitted into the tapered distal bore 178 of the proximal femoral body 168. The proximal femoral body 168 can be attached to the distal stem 126 using a fastener 188 that can be slid through the bore 170 of the proximal femoral body and can threadingly engage the inner cylindrical surface 156 of the distal stem 126.

Moreover, the foregoing discussion discloses and describes merely exemplary embodiments of the present disclosure. One skilled in the art will readily recognize from such discussion, and from the accompanying drawings and claims, that various changes, modifications and variations can be made therein without departing from the spirit and scope of the disclosure as defined in the following claims. For instance, the sequence of the blocks of the method described herein can be changed without departing from the scope of the present disclosure.

What is claimed is:

1. A method of implanting a modular prosthetic component, comprising:
    attaching a guide rod to the prosthetic component; removably coupling the guide rod to a shaft extending from a handle; positioning the prosthetic component in an anatomical feature; impacting an impaction portion of the handle; and uncoupling the guide rod from the shaft to remove the shaft, leaving the guide rod attached to the prosthetic component; wherein removably coupling the guide rod to a shaft includes operating a coupling mechanism that includes a sleeve that captures at least one ball bearing in at least one hole extending transversely through the shaft, at least one pin that extends through at least one slot in the shaft to axially fix the sleeve to the shaft within the at least one slot, and a biasing member that axially biases the sleeve relative to the shaft.

2. The method of claim 1, further comprising attaching the guide rod to the prosthetic component by threading the guide rod into the prosthetic component.

3. The method of claim 1, further comprising rotationally fixing the guide rod to the handle.

4. The method of claim 3, further comprising threading the guide rod into the prosthetic component using the handle.

5. The method of claim 1, further comprising impacting the impaction portion of the handle until the prosthetic component is driven to a desired depth in the anatomical feature.

6. The method of claim 5, further comprising using numbered indicia on the shaft to determine when the prosthetic component is driven to the desired depth.

7. The method of claim 1, further comprising impacting a striker plate that is fixed to the shaft to remove the prosthetic component from the anatomical feature when the prosthetic component is misaligned with respect to the anatomical feature.

8. The method of claim 1, wherein operating the coupling mechanism includes using a quick connect mechanism.

9. The method of claim 8, wherein removably coupling the guide rod to the shaft includes: axially retracting a sleeve of the quick connect mechanism, placing the shaft over the guide rod to insert the guide rod into a hole in the shaft, and releasing the sleeve.

10. The method of claim 9, further comprising uncoupling the guide rod from the shaft by axially retracting the sleeve and pulling the shaft from the guide rod to remove the guide rod from the hole in the shaft.

11. The method of claim 1, further comprising positioning a reamer over the guide rod to create a reamed opening in the anatomical feature.

12. The method of claim 11, further comprising removing the reamer from the reamed opening and placing a proximal body over the prosthetic component, wherein the prosthetic component is a distal stem.

13. The method of claim 11, further comprising sliding the reamer over the guide rod until a flat annular surface on the reamer abuts a flat annular surface on the guide rod.

14. The method of claim 13, further comprising verifying that an indicia on the guide rod is visible through a hole in the reamer to ensure that the flat annular surface on the reamer is abutting the flat annular surface on the guide rod.

15. A method of implanting a modular prosthetic component, comprising:
axially retracting a spring-loaded sleeve of an inserter assembly; inserting a guide rod into a hollow shaft of the inserter assembly; releasing the spring-loaded sleeve to couple the guide rod to the shaft; rotating a handle fixed to the hollow shaft to thread the guide rod into a distal stem; positioning the distal stem in an intramedullary canal of a femur;
impacting an impaction portion of the handle; axially retracting the spring-loaded sleeve; and pulling the handle to remove the inserter assembly from the guide rod, leaving the guide rod attached to the distal stem; wherein releasing the spring-loaded sleeve to couple the guide rod to the shaft includes operating a coupling mechanism wherein the spring-loaded sleeve captures at least one ball bearing in at least one hole extending transversely through the shaft, at least one pin that extends through at least one slot in the shaft to axially fix the sleeve to the shaft within the at least one slot, and a biasing member that axially biases the sleeve relative to the shaft.

16. The method of claim 15, further comprising impacting the distal stem to a selected depth in the intramedullary canal using numbered indicia on the shaft.

17. The method of claim 15, further comprising positioning a reamer over the guide rod to create a reamed opening in the femur.

18. The method of claim 17, further comprising removing the reamer from the reamed opening, unthreading the guide rod from the distal stem, and connecting a proximal body to the distal stem.

19. A method of implanting a modular prosthetic component, comprising: inserting a guide rod into a bore of a hollow shaft of an inserter assembly while holding a quick connect mechanism of the inserter assembly in a first position; moving the quick connect mechanism of the inserter assembly to a second position to at least axially fix and connect the guide rod within the bore of the hollow shaft; rotating a handle fixed to the hollow shaft to threadably engage the guide rod to a distal stem; impacting an impaction portion of the handle to position the distal stem into an intramedullary canal of a femur; moving the quick connect mechanism of the inserter assembly to the first position a second time to at least axially disengage the guide rod from the inserter assembly; while holding the quick connect mechanism of the inserter assembly in the first position at the second time, pulling the handle to remove the inserter assembly from the guide rod and leaving the guide rod attached to the distal stem; positioning a reamer over the guide rod and creating a reamed opening in the femur by guiding the reamer with the guide rod to create the reamed opening in a proximal portion of the femur for placement of a proximal body; removing the reamer from the reamed opening; unthreading the guide rod from the distal stem; and connecting the proximal body to the distal stem, wherein the quick connect mechanism includes a sleeve that captures at least one ball bearing in at least one hole extending transversely through the shaft, at least one pin that extends through at least one slot in the shaft to axially fix the sleeve to the shaft within the at least one slot, and a biasing member that axially biases the sleeve relative to the shaft.

* * * * *